United States Patent [19]

Suciu et al.

[11] 4,227,537
[45] Oct. 14, 1980

[54] ENDOMETRIAL BRUSH WITH SLIDABLE PROTECTIVE SLEEVE

[75] Inventors: Thomas N. Suciu; Herbert J. Schmidt, both of Tucson, Ariz.

[73] Assignee: Tucson Medical Instruments, Inc., Tucson, Ariz.

[21] Appl. No.: 884,634

[22] Filed: Mar. 8, 1978

[51] Int. Cl.³ .................... A61B 1/00; A61B 10/00
[52] U.S. Cl. ................................ 128/756; 128/357
[58] Field of Search .................... 73/425, 425.2; 15/104.165, 104.2, 145, 169, 168, 184, 206; 128/2 B, 2 N, 269, DIG. 14, 256, 357

[56] References Cited

U.S. PATENT DOCUMENTS

| | | | |
|---|---|---|---|
| 1,967,597 | 7/1934 | Schwartz | 15/206 |
| 2,955,591 | 10/1960 | MacLean | 128/2 B |
| 3,877,464 | 4/1975 | Vermes | 128/2 B |
| 3,998,216 | 12/1976 | Hosono | 128/6 |
| 4,048,998 | 9/1977 | Nigro | 128/263 |
| 4,108,162 | 8/1978 | Chikashige | 128/2 W |
| 4,127,113 | 11/1978 | Nollan | 128/2 B |
| 4,136,680 | 1/1979 | Southworth | 128/213 |

FOREIGN PATENT DOCUMENTS

| | | | |
|---|---|---|---|
| 671738 | 9/1929 | France | 15/206 |
| 2305959 | 10/1976 | France | 128/2 B |
| 1394925 | 5/1975 | United Kingdom | 128/2 W |

OTHER PUBLICATIONS

Webster's Dictionary, G & C Merriam Co., Springfield, Mass., 1963, p. 648, "plastic".
"Expanded PTFE: It's A Whole New Ballgame", Plastics World, Jul., 1971.

*Primary Examiner*—Robert W. Michell
*Assistant Examiner*—J. L. Kruter
*Attorney, Agent, or Firm*—Cahill, Sutton & Thomas

[57] ABSTRACT

An endometrial brush and method of using, the endometrial brush including a slidable protective sleeve for protecting bristles of the endometrial brush from wetting and contamination by cervical tissue during insertion of the endometrial brush through the cervix and into the endometrial cavity of the patient. The protective sleeve is composed of tubular flexible material which is slid forward along a shaft of the endometrial brush to cover the bristles during insertion. After the bristle section of the brush is in its desired position in the endometrial cavity, the protective sleeve is slid backward along the shaft, thereby uncovering the bristles. The handle is then manipulated to cause the bristles to scrape the walls of the endometrial cavity, thereby collecting sample tissue and/or cells. The brush is then withdrawn through the cervix. The collected sample is smeared on a microscope slide and analyzed.

12 Claims, 15 Drawing Figures

U.S. Patent   Oct. 14, 1980   Sheet 1 of 2   4,227,537
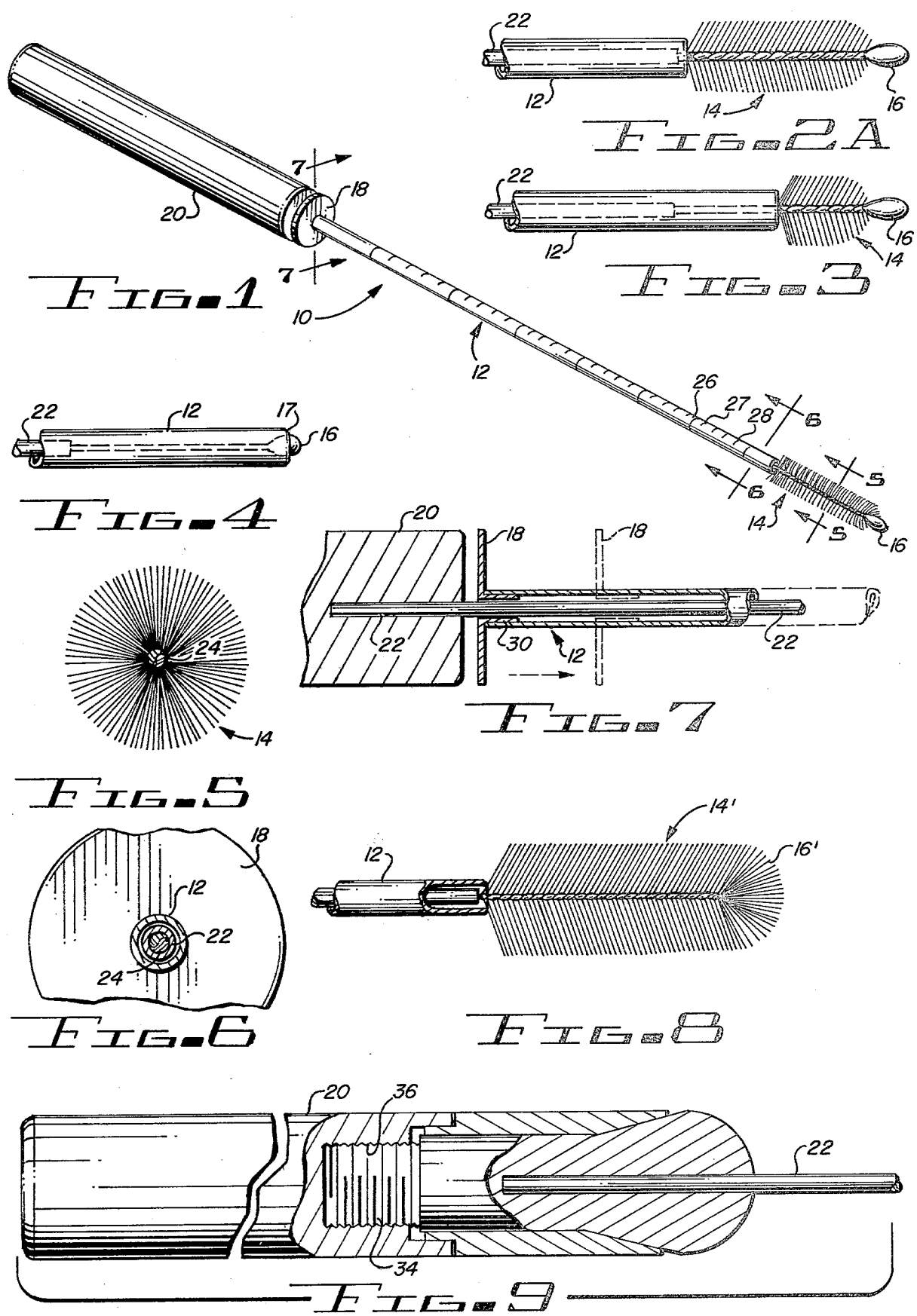

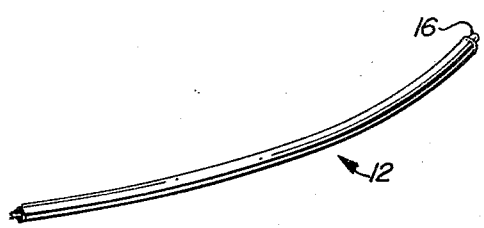
FIG.-10B
FIG.-10A
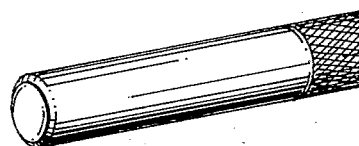
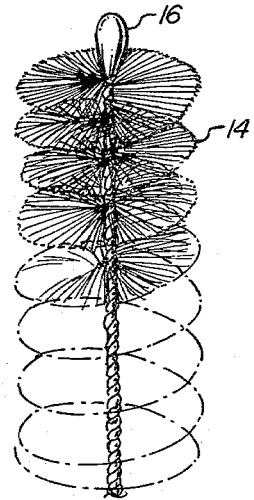
FIG.-2B
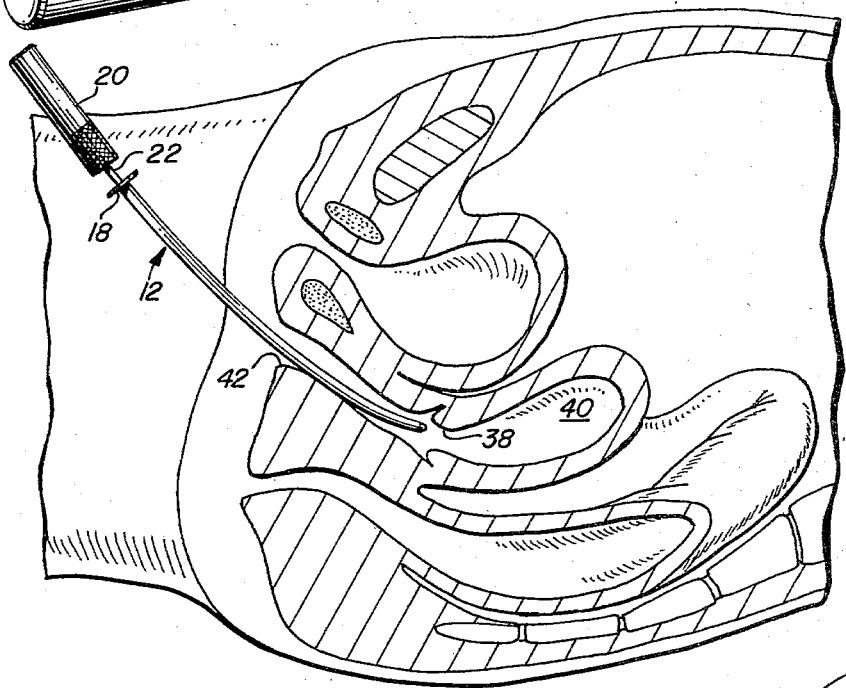
FIG.-11A
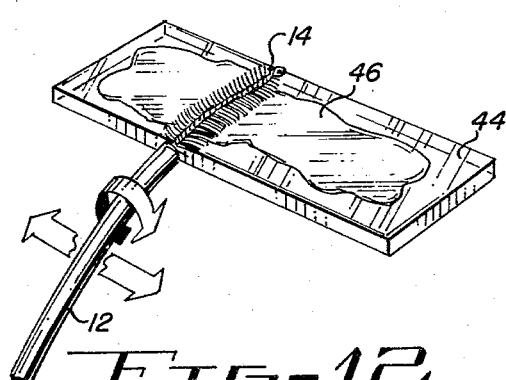
FIG.-12
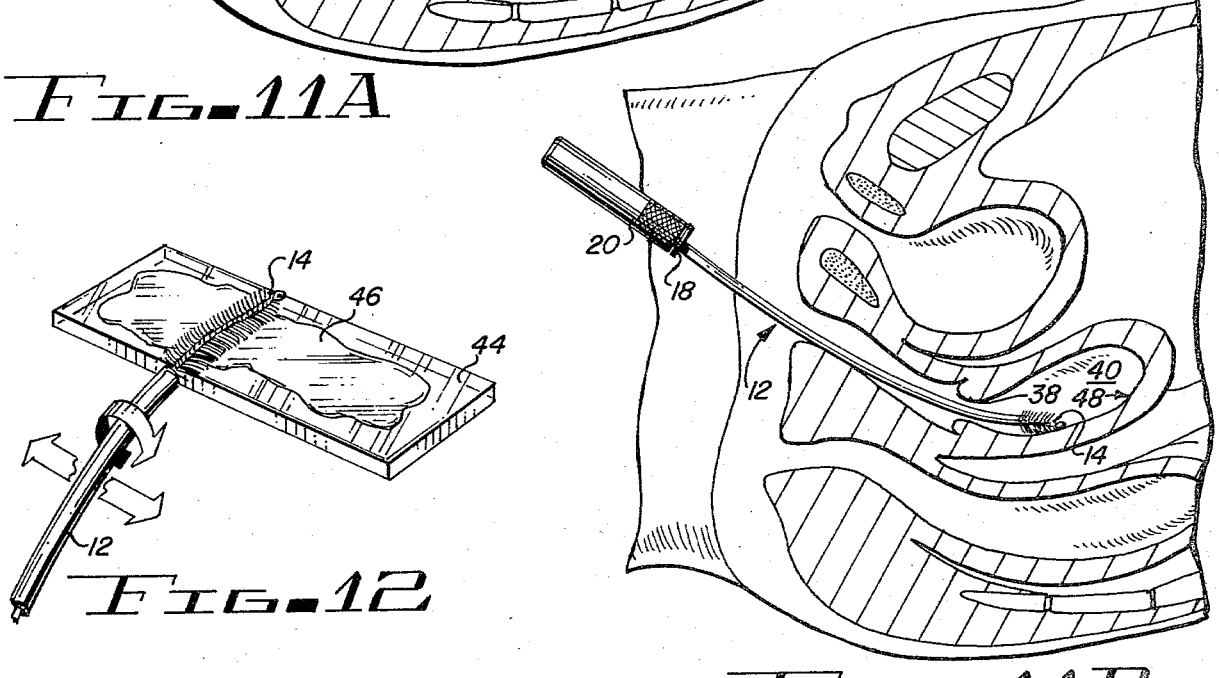
FIG.-11B

ENDOMETRIAL BRUSH WITH SLIDABLE PROTECTIVE SLEEVE

BACKGROUND OF THE INVENTION

1. Field of the Invention

The invention relates to brushes and methods for collecting sample tissue from an endometrial cavity to aid diagnosing of endometrial cancer.

2. Description of the Prior Art

For a number of years, the incidence of cervical cancer was greater than the incidence of endometrial cancer. In order to diagnose cervical cancer a reliable, inexpensive treatment, the well-known Pap test, is widely utilized to diagnose cervical cancer. The Pap test is widely accepted by physicians and patients because of its reliability, low cost, convenience of application, and painlessness. Patients are not hesitant to periodically submit to the Pap test. Consequently, cervical cancer is usually diagnosed sufficiently early to be effectively treated. As a result of such effective treatment, the incidence of cervical cancer has become smaller than the incidence of endometrial cancer. This has occurred because until now, reliable, convenient, inexpensive, relatively painless methods and devices for obtaining samples of endometrial tissue and cells have not been available.

One known collecting device for endometrial cell and tissue samples, called a Medoza Canula, includes a curved plastic stem to facilitate its insertion into an endometrial cavity and a head having annular plastic flanges which operate to scrape cells from the walls of the endometrial cavity. The Medoza Canula includes a retractable protective sleeve to cover the head and the plastic flanges thereof to prevent wetting and contamination during insertion of the device through the patient's cervix. Once the head of the Medoza Canula is properly positioned in the endometrial cavity, the protective sleeve is retracted, exposing the plastic flanges. The handle is then manipulated forward and backward to cause the plastic flanges to scrape cells and tissue from the walls of the endometrial cavity. However, the Medoza Canula has a fixed depth limiting member which limits the depth of penetration of the head into the endometrial cavity. Consequently, for some patients the plastic flanges do not reach sufficiently deeply into the endometrial cavity to collect sample cells or tissue for analysis. Another disadvantage of the Medoza Canula is that the plastic flanges do not scrape the walls of the endometrial cavity sufficiently effectively to collect all of the cells and tissue which should be analyzed for presence of cancerous cells. The plastic flanges do not effectively scrape loose tissue and cells in response to rotation of the handle. Further, the plastic flanges "pick up" loose cells, but do not effectively scrape or pick up cells or tissue which is very deep within the endometrial walls. This prevents analysis of a suitably broad spectrum of potentially cancerous cells which might be present in the tissue of the endometrial walls. Further, the adherance of scraped cells to the plastic flanges of the Medoza Canula is thought to be inadequate to ensure retention of such cells on the flanges during withdrawal of the head through the cervix. Finally, the plastic flanges of the Medoza Canula do not efficiently collect sample tissue and cells from the deepest portions of the endometrial cavity. This is a serious shortcoming, because endometrial cancer frequently begins its growth in the deepest portions of the endometrial cavity.

Another known collecting device for endometrial cell and tissue samples is disposed in U.S. Pat. No. 3,945,372, by Milan et al, issued Mar. 23, 1976. The endometrial tissue obtaining instrument described in the Milan et al patent includes a handle and a plastic spiral section which is inserted into the endometrium and rotated to collect endometrial tissue. This device does not have a protective sleeve, as does the above Medoza Canula. It is believed that the device of the Milan et al patent has the same general shortcomings as the above-described Medoza Canula, and additionally has the shortcoming that wetting of the spiral section occurs during insertion, thereby substantially reducing the adherance of endometrial tissue to the spiral section. It is also believed that the spiral section does not dig sufficiently deeply into the endometrial walls to collect as wide a spectrum of possibly cancerous cells and tissues as is desirable.

Other methods of collecting endometrial cells and tissue include aspirator type devices (which operate to suck cells from the endometrial walls) and a type of device referred to as a "gravely jet washer". Both of these types of devices require expensive motor driven mechanisms. Such machines are not ordinarily available in a physicians office. In both types of devices, the collected cells are collected in a fluid, which must be strained through a filter in order to collect the cells so that they can be placed on a microscope slide by analysis. This type of procedure is not of a type which can be economically routinely performed in a typical physicians office.

It is an object of the invention to provide an inexpensive, efficient method of obtaining samples of endometrial cells and/or tissue.

It is another object of the invention to provide a method of obtaining endometrial tissue and cell samples which can be easily placed on a microscope slide for analysis.

It is another object of the invention to provide a method of obtaining endometrial tissue which is sufficiently uncontaminated to permit accurate diagnosis of endometrial cancer.

It is another object of the invention to provide an endometrial brush which may be inserted with minimum discomfort to the patient.

It is another object of the invention to provide an inexpensive endometrial brush which efficiently collects a broad spectrum of endometrial tissue and cell samples.

It is another object of the invention to provide an inexpensive endometrial brush which avoids wetting and/or contamination of its bristles during insertion and withdrawal of the endometrial brush.

It is another object of the invention to provide an endometrial brush to efficiently collect endometrial tissue and/or cell samples from the deepest portions of an endometrial cavity.

Briefly described, and in accordance with one embodiment thereof, the invention provides an endometrial brush and method for efficiently and inexpensively collecting samples of endometrial tissue and/or cells from the walls of a patient's endometrial cavity. The endometrial brush includes a handle, which may be permanently or detachably connected to a semi-rigid shaft. A flexible, slidable sleeve is provided on the shaft and can be slid forward along the shaft to cover the bristles of the brush during insertion and withdrawal and can be slid backward along the shaft to uncover the bristles in the endometrial cavity to permit scraping of sample tissue and cells therefrom. The semi-rigid shaft may be bent so that it conforms to the curvature of the passage through the vagina, cervix, and endometrial cavity of an individual patient. The shaft, when so bent, maintains its bent configuration so that when the endometrial brush is fully inserted, the bristles of the brush are suitably positioned for scraping and collecting sample tissue and cells from the endometrial walls. The bristles are helically wound to form a helix along a segment of the shaft furthest from the handle. A small, rounded bead is connected to the extreme end of the shaft beyond the bristles. The diameter of the bead is sufficiently small to permit insertion of the endometrial brush through the patient's cervix with minimum discomfort to the patient. The bead forms a seal with the inner surface of the flexible sleeve when the sleeve is slid forward to cover the bristles during insertion and withdrawal of the endometrial brush. In one embodiment of the invention, the rounded bead is omitted, and a group of end bristles fanning outwardly from the end of the shaft is provided to more efficiently scrape tissue and cell samples from the deepest portions of the endometrial cavity, where the probability of cancerous tissue and cells may be highest. According to the invention, the slidable sleeve is deployed to prevent the bristles from becoming "saturated" or wetted with moisture and tissue from the vaginal canal and cervical passage during insertion of the endometrial brush. After the bristles are uncovered in the endometrial cavity, the handle of the endometrial brush is then rotated and moved longitudinally to cause the bristles to "dig into" the endometrial walls to scrape a broad spectrum of cells and tissue therefrom. The sleeve is then deployed to cover the bristles, the endometrial brush is then withdrawn, and the sleeve is again retracted. The sample tissue and cells on the bristles are then wiped onto a microscope slide for immediate analysis. The endometrial brush may be discarded or sterilized for later use. In one embodiment of the invention, the handle is detachable from the shaft; the shaft and bristles thereof are disposable.

BRIEF DESCRIPTION OF THE DRAWINGS

FIG. 1 is a perspective view of one embodiment of endometrial brush of the invention.

FIG. 2A is a partial view of the bristle and shaft portion of the endometrial brush of FIG. 1.

FIG. 2B is a perspective view of the bristle section of the brush of FIGS. 1 and 2A illustrating the preferred helical nature of the bristle section.

FIG. 3 is a diagram illustrating the protective sleeve partially deployed to cover a portion of the bristles of the endometrial brush of FIG. 1.

FIG. 4 is a partial view of endometrial brush of FIG. 1 showing the protective sleeve deployed to entirely cover the bristle section.

FIG. 5 is a sectional view taken along section lines 5—5 of FIG. 1.

FIG. 6 is a partial sectional view taken along section lines 6—6 of FIG. 1.

FIG. 7 is a partial sectional diagram taken along section lines 7—7 of FIG. 1.

FIG. 8 is a partial cutaway view showing an alternate bristle configuration for the endometrial brush of FIG. 1.

FIG. 9 is a partial cutaway view showing a mechanism for permitting removal of the shaft section from the handle section of the endometrial brush.

FIG. 10A is a perspective view showing the configuration of the endometrial brush with the shaft bent prior to the utilization.

FIG. 10B illustrates the shaft section bent with the sleeve deployed to cover the bristle section and form a seal with the end bead.

FIG. 11A illustrates insertion of the endometrial brush of FIG. 10A into the cervical passage.

FIG. 11B illustrates deployment of the endometrial brush of FIG. 10A bristles exposed in the endometrium.

FIG. 12 illustrates rotation and longitudinal movement of the endometrial brush to smear the collected endometrial sample on a microscope slide.

DESCRIPTION OF THE INVENTION

Referring now to the drawings, and particularly to FIGS. 1-7, endometrial brush 10 includes a handle 20, a slidable, flexible sleeve 12 disposed about a rigid but bendable shaft 22, and a cylindrical, preferably helically wound, bristle brush 14 disposed at the end of shaft 22. The helically wound bristles 14 are more clearly illustrated in FIG. 2B. Sleeve 12 is manually slidable along shaft 22 to expose or cover bristles 14 by means of flanged disc 18, as indicated in FIGS. 1 and 7. The physician can slide sleeve 12 forward by using the thumb and first digit of his hand holding handle 20 to move disc 18 and sleeve 12 forward along shaft 22, as indicated by the arrow in FIG. 7, thereby covering bristles 14 and achieving a sealing relationship with rounded bead 16. Sleeve 12 may be made of teflon. Handle 20 may be molded plastic. Bristles 14 may be made of nylon or natural bristle, such as boar bristle.

Bead 16 is disposed on the end of wound wire portion 24 of shaft 22. Rounded bead 16 sealably fits within the interior of flexible sleeve 12 when sleeve 12 is slid forward as indicated in FIG. 4, so as to protect bristles 14 from wetting and contamination of bristles 14 by moisture and cervical tissue during insertion of endometrial brush 10 through the cervix of a patient. Rounded bead 16 also prevents discomfort to the patient during the insertion of endometrial brush 10 through the cervix and into the endometrial cavity. Edge 17 of sleeve 12 is slightly rounded, as indicated by reference numeral 17 in FIG. 4, to minimize discomfort to the patient during insertion. Rounded bead 16 may be made of plastic or other suitable material.

In a presently preferred embodiment of the invention the outside diameters of helically wound bristle section 14 is slightly over one fourth of an inch. The outside diameter of rounded bead 16 is approximately 0.125 inches of an inch. The length of the section including shaft 22 (but not any part of shaft 22 buried in handle 20) and bristles 14 is approximately seven inches; the length of bristle section 14 is approximately one inch. Handle 20 is approximately three and one half inches long. However, these dimensions may be varied to suit varying requirements.

A wound wire shaft supporting bristles 14 is inserted into an open end of shaft 22, which may be composed of metal tubing having an outside diameter of approximately 0.093 inches and an inside diameter of approximately 0.062 inches. FIG. 6 shows a cross-sectional view of flexible sleeve 12, semi-rigid shaft 22, and wound wire bristle-supporting shaft 24 taken along section lines 6—6 of FIG. 1.

An alternate embodiment of the bristle section 14 is shown in FIG. 8, wherein a hemispherical end section 16' of bristles is provided at the extreme end of the wound wire bristle supporting shaft in place of rounded bead 16. The preferred helical winding of the bristles 14 is illustrated in the perspective view of FIG. 2B. The embodiment of FIG. 8 may be more desirable in certain cases for probing the deepest portions of the endometrial cavity to collect tissue and cell samples therefrom, but is somewhat more subject to wetting and contamination during insertion of the endometrial brush than the embodiment of FIGS. 1-4, and is more likely to cause discomfort to the patient during insertion through the cervix.

As explained subsequently, it is desirable that shaft 22 be semi-rigid, so that the physician can, after determining the contour of the uterous of an individual patient, bend the shaft 22 so that it remains bent, as indicated in FIGS. 10A and 10B, to facilitate scraping of tissue from the desired portions of the walls of the endometrial cavity.

It is anticipated that the endometrial brush 10 of the present invention will be most useful to physicians in furthering the art of diagnosing endometrial cancer if the endometrial brush is inexpensive and disposable, since the problems and inconvenience associated with sterilizing and cleaning the endometrial brushes after use is rather impractical and uneconomical in a typical physician's office, where diagnosis of uterine cancer is ordinarily preferably made. However, FIG. 9 discloses an alternate embodiment of the invention having a disposable brush and shaft section and a permanent handle section which can be removably engaged with the disposable brush and shaft section. Alternately, the sleeve can be discarded and the shaft and attached bristles can be cleaned, sterilized, and re-used with a new sterile sleeve.

A graded scale is preferably provided on flexible sleeve 12, as indicated in FIG. 1 by reference numerals 26, 27, and 28, so that the physician can readily determine how far endometrial brush 10 has been inserted into the uterine cavity before the sleeve is retracted to permit collecting of the tissue and cell sample. The graded scale eliminates the need for the physician to initially utilize a separate uterine sound to measure the uterus before deploying the endometrial brush.

FIGS. 11A and 11B illustrate the insertion of a previously bent endometrial brush (as indicated in FIG. 10A) through vagina 42 and cervix 38 into endometrial cavity 40. FIG. 11A shows the rounded bead portion of the endometrial brush about to enter cervix 38; slidable sleeve 12 and flange disc 18 are in the forward position so that a moisture-proof seal is provided between the end of flexible sleeve 12 and rounded bead 38.

FIG. 11B shows the endometrial brush inserted into endometrial cavity 40 with flexible sleeve 12 and optional flanged disc 18 retracted to expose bristles 14. The endometrial sample is then collected.

Referring to FIGS. 11A and 11B, the method of utilizing endometrial brush 10 to obtain accurate cytologic interpretation of the endometrium is as follows. First, endometrial brush 10 is removed from a sterile package. If a non-disposable handle is utilized, the shaft and brush section is connected to the handle. Protective sleeve 12 is then advanced over bristles 14 and rounded bead 16 to protect bristles 14 from wetting and contamination during insertion through the patient's cervix 38; a speculum can be utilized in the usual manner.

Optionally, the cervix may be cleansed with an antiseptic solution. Endometrial brush 10 is inserted through cervic 38 into the endometrial cavity 40 until it reaches the fundal or top portion 48 of the uterus, whereat a slight resistance to further inward movement of brush 10 is encountered.

The position of bristles 14 is maintained by holding handle 20 stationary and sliding protective sleeve 12 along the shaft toward the handle by means of control disc 18, thereby exposing bristles 14 at the desired location within endometrial cavity 40.

An individual patient's cervix may be "tipped" either forward or backward. Semi-rigid shaft 22 of endometrial brush 10 is therefore bent in accordance with the contour of the individual patient's uterous so that the sleeve, shaft, etc., may be inserted through the cervix with minimum discomfort to that patient and so that bristles 14 will be properly positioned when the insertion of the endometrial brush is complete.

Handle 20 is then manipulated by rotating it and longitudinally moving it so that the desired portions of the walls and fundal portion of the endometrium are scraped by the helical bristles 14 to collect sample tissue and cells therefrom.

Endometrial brush 10 is then withdrawn straight out of the uterine cavity, with the sleeve still advanced, as shown in FIG. 11B. In most cases, it is preferable not to advance sleeve 12 over the bristles 14 and rounded bead 16 prior to withdrawal of the endometrial brush 10 because this would scrape much of the collected cell and tissue sample off of bristles 14. Contamination of the collected cell and tissue sample by cervical cells and tissue during withdrawal ordinarily causes no difficulty, since endometrial cancer cells are usually recognizably different than cervical cancer cells. Since bristles 14 are already saturated by endometrial cells and tissue at this stage of the method, very few cervical cells will become affixed to the bristles during withdrawal through the cervix. Withdrawal of the endometrial brush 10 usually causes very little discomfort to the patient, even with bristles 14 exposed.

Bristles 14 are then smeared directly on glass slide 44 by rotating the brush and streaking it longitudinally as indicated in FIG. 12. This is a more convenient technique than that described in the above Milan et al patent, and ensures a broad spectrum of the cells and/or tissue collected from various parts of the endometrium are available on the slide 44 for analysis. Glass slide 44 and sample 46 are then immediately placed in ninety-five percent alcohol fixative and submitted for staining by the well-known Papanicolau technique. Further analysis is completely conventional, and will not be described herein.

Adenocarcinoma of the endometrium is now accepted as the most common female genital neoplasm. This change in relative frequency between cervical cancer and endometrial cancer may be attributed to several factors. Foremost among these factors has been the development of cytologic screening techniques for cervical cancer, widespread acceptance by physicians and patients of these techniques, and their wide spread utilization in typical doctor's offices.

The endometrial brush 10 disclosed herein should permit the significant advances in the field of cytology and cytotechnology to be applied to the interpretation of endometrial cytology by providing adequate specimens for analysis. By using the foregoing endometrial brush and method, endometrial specimens for analysis may be readily collected on a routine basis. The simple and reliable collecting technique involves minimal expense and discomfort to the patient, and should meet with both physician and patient acceptance.

The avoidance of wetting or saturation of the bristles of the endometrial brush of the present invention during insertion thereof through the cervix ensures that the bristles will be dry when exposed. The dry bristles can scrape the desired cells and tissue from the endometrial walls much more effectively than if the bristles are wet. Well established procedures which are routine in any gynecologist's or obstetrician's office are readily applicable. The inconvenience and high cost of the aspirator type devices and the gravely jet washer type devices previously used for collecting endometrial tissue and cell samples are overcome by the present endometrial brush and method of use. The helical bristles of the inventive endometrial brush also are believed to scrape cells and tissue from the endometrial walls, especially of the fundal portion of the endometrium, more efficiently than the previously described Medoza Canula, which has radial flanges or fins, and therefore must be moved forward and backward in order to collect a sample. The helical bristles are also believed to scrape cells from the endometrial walls more efficiently than the device of the Milan et al patent because the helical bristles individually dig into the endometrial walls. It is further believed that the wetting of the spiral section of the Milan et al device and the smoothness of the entire spiral section thereof prevent adherence of the collected endometrial sample to the degree that such adherence is achieved for the helical bristles of the present invention.

Variations of the slidable protective sleeve are within the scope of the present invention. For example, the protective sleeve may have a closed end portion which is closed during insertion, and is then opened by penetration of the end of the shaft and the bristles thereon by sliding the protective sleeve toward the handle after insertion into the endometrium. In another embodiment of the invention, shaft 22 is flexible and sleeve 12 is semi-rigid. In this case, the flexible shaft 22 is rotated within the semi-rigid sleeve by means of the handle to cause the bristles to rotate inside the endometrial cavity.

What is claimed is:

1. An endometrial brush for obtaining endometrial samples, said endometrial brush comprising in combination:
   (a) a handle for manipulating said endometrial brush;
   (b) a shaft having first and second end portions, the first end portion being attached to said handle, said shaft being rigid and bendable so that when said shaft is bent to a particular configuration, said shaft rigidly retains that configuration;
   (c) a plurality of bristles attached to the second end portion of said shaft for collecting said endometrial sample, said bristles being oriented about the second end portion of said shaft to form a bristle section;
   (d) a flexible sleeve slidably disposed on said shaft for covering said bristles during insertion of said endometrial brush into a patient's endometrium and exposing said bristles within the endometrium to permit scraping of cells and tissue from the endometrium by said bristles, said flexible sleeve having an outside diameter sufficiently small to enable insertion of said endometrial brush into the endometrium of the patient without substantial discomfort to the patient;
   (e) first means connected to said sleeve for effecting sliding said sleeve along said shaft to cover said bristles during said insertion and sliding of said sleeve along said shaft to expose said bristles after said bristles are properly positioned in the endometrium; and
   (f) rounded means attached to the end of said shaft for minimizing discomfort to the patient during insertion of said endometrial brush, wherein said sleeve sealably engages said rounded means if said sleeve is slid along said shaft so that one end of said sleeve slides over said bristles and over said rounded means, whereby no moisture, tissue, or cells contact said bristles during insertion of said endometrial brush.

2. The endometrial brush of claim 1 wherein said first means includes a flanged disc axially disposed on said shaft, said flanged disc having a disc portion which is easily grasped by a finger and thumb of the user of said endometrial brush, said flanged disc also having a flange portion for engaging said sleeve.

3. The endometrial brush of claim 1 wherein said sleeve is composed of flexible material.

4. The endometrial brush of claim 3 wherein said sleeve has a rounded edge to minimize discomfort to the patient during insertion of said endometrial brush.

5. The endometrial brush of claim 1 wherein said handle is composed of plastic.

6. The endometrial brush of claim 1 wherein said shaft is detachable from said handle.

7. The endometrial brush of claim 1 wherein said shaft is composed of brass tubing.

8. The endometrial brush of claim 1 wherein said bristles are supported by a wound wire shaft having an end thereof attached to the second end of said shaft.

9. The endometrial brush of claim 1 wherein said rounded means includes a plastic bead.

10. The endometrial brush of claim 1 wherein said rounded means includes a metal bead.

11. The endometrial brush of claim 1 wherein said bristles are composed of synthetic nylon bristles.

12. The endometrial brush of claim 1 wherein:
   (a) said bristles form a substantially cylindrical brush portion of said endometrial brush, said cylindrical brush portion having a diameter of approximately one fourth inch;
   (b) said sleeve has an outside diameter of approximately 0.125 inches;
   (c) said rounded means has an outside diameter of approximately 0.125 inches.

* * * * *